(12) United States Patent
Henschel et al.

(10) Patent No.: US 11,969,302 B2
(45) Date of Patent: Apr. 30, 2024

(54) HEADER HAVING RADIOGRAPHIC MARKER

(71) Applicant: BIOTRONIK SE & CO. KG, Berlin (DE)

(72) Inventors: Martin Henschel, Berlin (DE); Marina Ruschel, Berlin (DE)

(73) Assignee: BIOTRONIK SE & Co. KG, Berlin (DE)

( * ) Notice: Subject to any disclaimer, the term of this patent is extended or adjusted under 35 U.S.C. 154(b) by 25 days.

(21) Appl. No.: 16/502,084

(22) Filed: Jul. 3, 2019

(65) Prior Publication Data
US 2020/0008900 A1  Jan. 9, 2020

(30) Foreign Application Priority Data

Jul. 6, 2018 (EP) ..................... 18182196

(51) Int. Cl.
| | | |
|---|---|---|
| *A61B 90/00* | (2016.01) | |
| *A61B 90/94* | (2016.01) | |
| *A61N 1/05* | (2006.01) | |
| *A61N 1/362* | (2006.01) | |
| *A61N 1/39* | (2006.01) | |

(52) U.S. Cl.
CPC .............. *A61B 90/39* (2016.02); *A61B 90/94* (2016.02); *A61N 1/05* (2013.01); *A61B 2090/3966* (2016.02); *A61N 1/362* (2013.01); *A61N 1/3956* (2013.01)

(58) Field of Classification Search
CPC . A61B 90/39; A61B 90/94; A61B 2090/3966; A61N 1/05; A61N 1/362; A61N 1/3956; A61N 1/3752; A61N 1/37229

USPC ..................... 600/431; 607/36, 122; 340/539
See application file for complete search history.

(56) References Cited

U.S. PATENT DOCUMENTS

| | | | | |
|---|---|---|---|---|
| 7,912,549 | B2 * | 3/2011 | Mueller | A61N 1/3752 607/36 |
| RE45,030 | E * | 7/2014 | Stevenson | A61B 90/98 340/539.12 |
| 9,808,617 | B2 | 11/2017 | Ostroff et al. | |
| 2009/0093855 | A1 | 4/2009 | Mueller et al. | |
| 2010/0275934 | A1 * | 11/2010 | Keren | G01D 5/2066 324/228 |
| 2012/0065503 | A1 * | 3/2012 | Rogers | A61B 90/94 600/431 |
| 2014/0058494 | A1 * | 2/2014 | Ostroff | A61N 1/0587 607/122 |
| 2017/0001021 | A1 | 1/2017 | Kane et al. | |
| 2017/0105810 | A1 * | 4/2017 | Wada | A61B 90/39 |
| 2017/0291029 | A1 * | 10/2017 | Khalil | A61N 1/37229 |
| 2017/0310059 | A1 | 10/2017 | Henschel et al. | |

FOREIGN PATENT DOCUMENTS

| | | | |
|---|---|---|---|
| EP | 3238778 A1 | 11/2017 | |
| WO | WO-2011143468 A2 * | 11/2011 | ......... A61B 18/1492 |

\* cited by examiner

*Primary Examiner* — Erin M Piateski
*Assistant Examiner* — Ranjani Mari Sundaresan
(74) *Attorney, Agent, or Firm* — Laurence A. Greenberg; Werner H. Stemer; Ralph E. Locher

(57) ABSTRACT

An electrode connector device for an implant. A radiographic marker is integrated in a metal conducting element. There is also described an implant with an electrode connector.

13 Claims, 2 Drawing Sheets

HEADER HAVING RADIOGRAPHIC MARKER

CROSS-REFERENCE TO RELATED APPLICATION

This application claims the priority, under 35 U.S.C. § 119, of European patent application EP 18182196.8, filed Jul. 6, 2018; the prior application is herewith incorporated by reference in its entirety.

BACKGROUND OF THE INVENTION

Field of the Invention

The disclosure relates to a header for an implant having a radiographic marker.

Generally, implants have radiographic markers. The marker is used to provide information about the implant, for example, the implant manufacturer. Based on the manufacturer information, a user (e.g., a physician) may select appropriate auxiliary equipment for the implant, for example, a compatible programming device.

As the packing density for electronics has increased, and as the products have decreased in size, however, it has become difficult to find mounting space in the implant for the radiographic marker that may also be uniquely detected under X-ray light.

Various options are known for providing radiographic markers. To wit:

United States patent application US 2017/310059 A1 and its European counterpart EP 3 238 778 A1 disclose an implant having a housing and a header. A radiographic marker is attached to a circuit board, wherein the circuit board is arranged in the header.

U.S. Pat. No. 7,912,549 B2 discloses an implant having a header. A cavity that receives a radiographic marker is formed in the header.

U.S. Pat. No. 9,808,617 B2 discloses a leadless pacemaker, wherein a radiographic marker is attached on the housing of the pacemaker.

According to U.S. patent application US 2017/0001021 A1, a radiographic marker is arranged as a separate component with a holder in the header or is printed on the header.

All of the known methods have in common that additional components are required for the radiographic marker and/or additional work steps must be carried out for producing the radiographic marker.

SUMMARY OF THE INVENTION

The object of the invention is to provide enhanced technologies for attaching a radiographic marker.

With the above and other objects in view there is provided, in accordance with the invention, an electrode connector device for an implant, the connector device comprising a metal conducting element and a radiographic marker integrated in said metal conducting element.

In other words, according to an aspect of the invention, an electrode connector device for an implant is provided, wherein a radiographic marker is integrated in a metal conducting element (e.g., a metal conducting ribbon or a metal conducting antenna).

The electrode connector device may also be referred to as connector head or header.

In accordance with an added feature of the invention, the connector device includes a receiving device for a connector, wherein said metal conducting element is a conductor connected to said receiving device and connectable to a feedthrough, and wherein said radiographic marker is integrated in said conductor.

The radiographic marker may be realized or designed, for example, as an element projecting from the conducting element. The radiographic marker may have or exhibit information about the manufacturer, type of device (e.g., pacemaker), and/or a serial number of the implant.

The radiographic marker may have or exhibit a graphic symbol, for example, an alphanumeric symbol. A plurality of alphanumeric symbols may be provided, as well. The radiographic marker may have or exhibit a combination of one or more graphic symbols with one or more alphanumeric symbols. In this way, it is possible to represent different information.

According to one aspect, an implant having an electrode connector device according to the features disclosed herein is provided.

The electrode connector device may have a receiving device for a connector, such as a connector of a lead or electrode. The receiving device may be connected to a conductor, wherein the conductor is connectable a feedthrough. The radiographic marker may be integrated in the conductor.

The electrode connector device may have a further receiving device for a further connector. The further receiving device may be connected to a further conductor, wherein the further conductor is connectable to the feedthrough. The radiographic marker may be integrated in the further conductor.

The electrode connector device may have an antenna. The radiographic marker may be integrated in the antenna. The antenna may have an antenna body that may have, for example, a meandering shape. The antenna may furthermore have an antenna connector that is connectable to a feedthrough. The radiographic marker may be integrated in the antenna body and/or in the antenna connector.

In one embodiment, the electrode connector device comprises a receiving device for a connector having a conductor and an antenna. The radiographic marker may be integrated in the conductor and/or in the antenna.

The implant may have a housing on which the electrode connector device is arranged. An electrical connection between components in the housing (e.g. an electronics module) and components in the electrode connector device (e.g. receiving device for a connector or antenna) may be established by means of a feedthrough. The feedthrough may have one or more plug-in contacts (e.g. pins) for connecting the conductor and/or the antenna. The radiographic marker may be formed on a side of the electrode connector device facing the housing (under side). Alternatively the radiographic marker may be formed on a side facing away from the housing (top side) or on a right or left side of the electrode connector device.

The electrode connector device may be or comprised within a header for an implantable pacemaker or an implantable cardioverter-defibrillator (ICD). In this case, the electrode connector device electrically connects one or more electrode leads to the implant.

The conducting element having the radiographic marker may be produced with various production methods, e.g., eroding, punching, or additive production methods such as laser sintering. The additional contour of the radiographic marker does not significantly increase the complexity of producing the conductive element (of the conductor/antenna), and punching does not increase the complexity at all.

A plurality of radiographic markers may be provided. The plurality of radiographic markers may be formed on the same conducting element. The receiving device may have a plurality of conductors (e.g. two, three, or four conductors). One radiographic marker may be formed on each of the plurality of conductors.

The conducting element (e.g. the conductor or the antenna) may made of a biocompatible metal, for example, niobium.

The conductive element and the radiographic marker may have a uniform thickness. It may be provided that the conductive element and/or the radiographic marker have a thickness of at least 50 µm. This ensures visibility during X-ray irradiation. The conductive element and/or the radiographic marker preferably have a thickness between 100 µm and 200 µm.

In addition to the radiographic marker, additional features may also be integrated in the conductive element (the conductor/antenna geometry) that may be used for positioning, testing, and handling, e.g. an index bore.

Other features which are considered as characteristic for the invention are set forth in the appended claims.

Although the invention is illustrated and described herein as embodied in a header having radiographic marker, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

BRIEF DESCRIPTION OF THE SEVERAL VIEWS OF THE DRAWING

Identical reference numerals are used for identical components throughout to figures of the drawing.

DETAILED DESCRIPTION OF THE INVENTION

Figure 1:
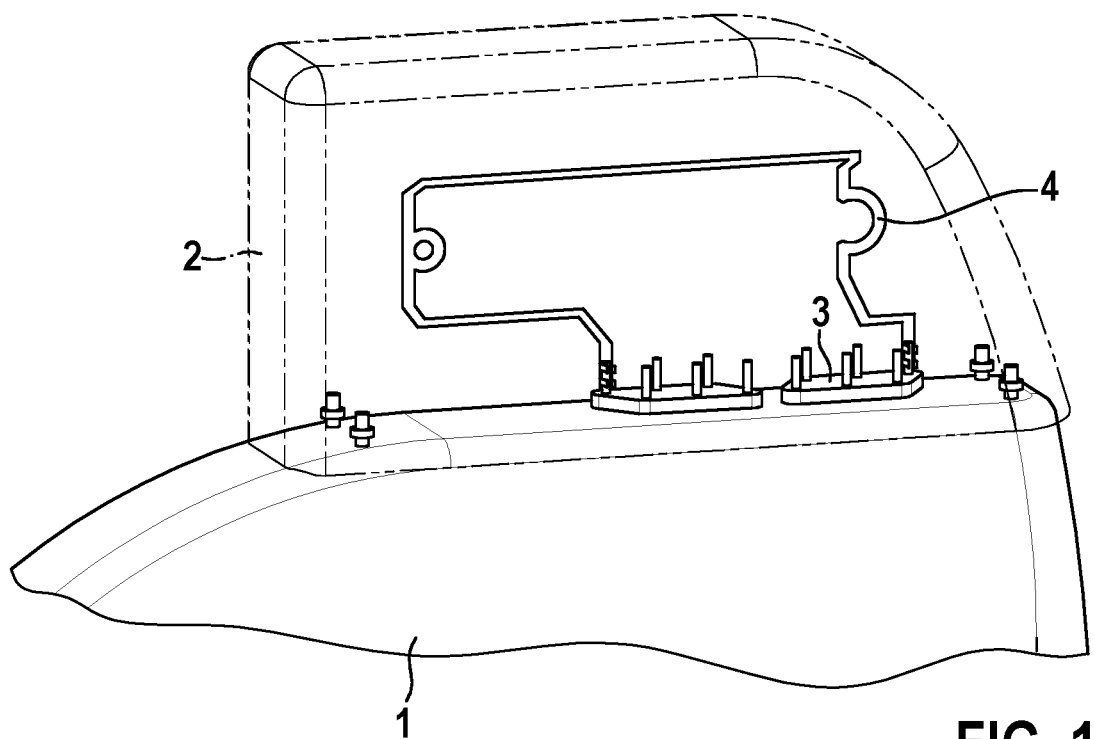
FIG. 1 is a perspective, partly broken away view of an implant having a header according to the prior art.

Referring now to the figures of the drawing in detail and first, particularly, to FIG. 1 thereof, there is shown an implant having a housing 1 on which an electrode connector device (header) 2 is arranged. A conventional antenna 4 is arranged in the electrode connector device 2. The antenna 4 is connected to electronic components in the housing 1 by way of a feedthrough 3.

Figure 2:
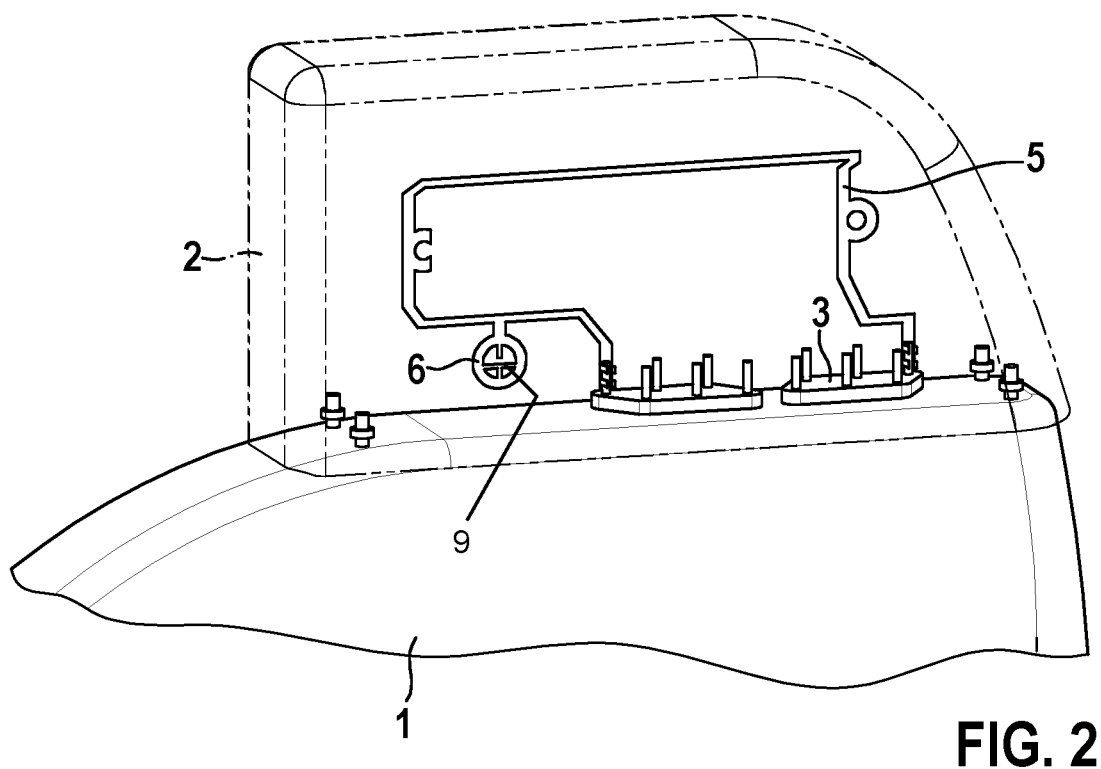
FIG. 2 is a similar view of an implant having a first exemplary embodiment of a header according to the invention.
Figure 3:
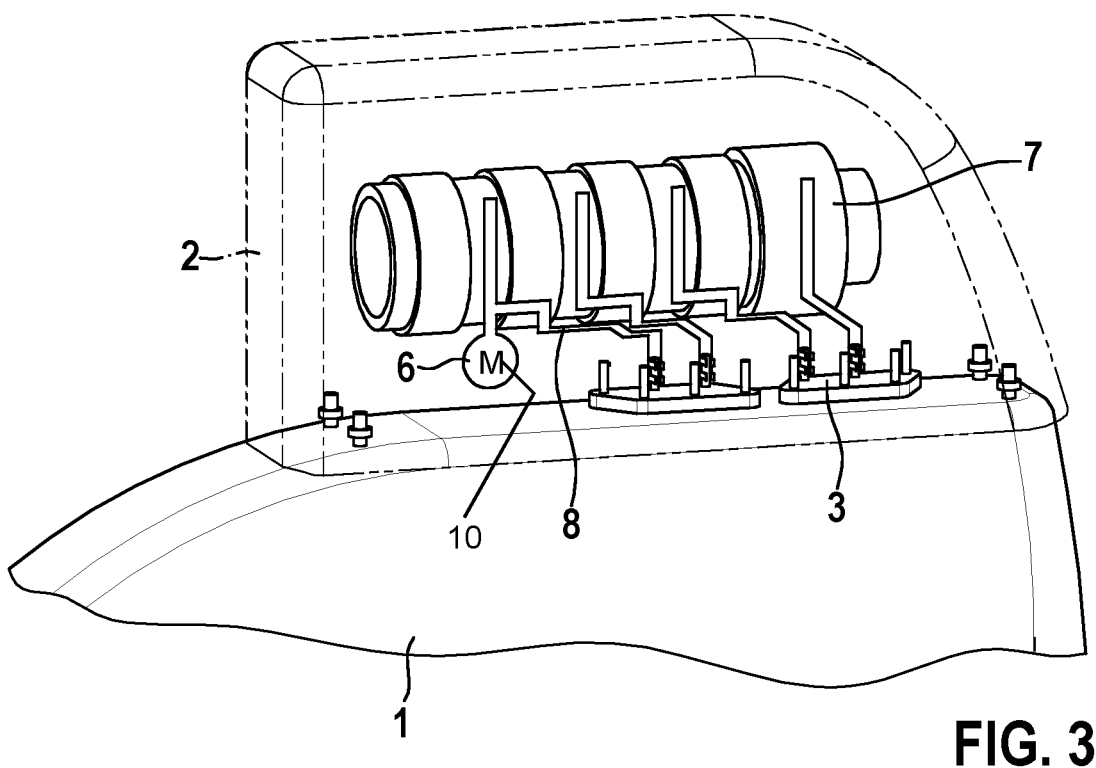
FIG. 3 is a similar perspective view showing an implant having a second exemplary embodiment of a header of the invention.

FIG. 2 shows an embodiment of the electrode connector device 2 according to the invention. An antenna 5 has an integrated radiographic marker 6. The radiographic marker 6 is realized as an element projecting from the antenna 5. The feedthrough 3 has a plurality of pins for connecting the antenna 5 and other components (FIG. 3). The radiographic marker 6 shown in FIG. 2 has a graphic symbol 9.

FIG. 3 shows another embodiment of an electrode connector device 2 according to the invention. A receiving device 7 for a connector is arranged in the electrode connector device 2. The receiving device 7 is connected to the feedthrough 3 by means of a conductor 8. The radiographic marker 6 is formed as an integral component of the conductor 8 and projects therefrom. The radiographic marker 6 shown in FIG. 3 has an alphanumeric symbol 10.

The teaching disclosed herein provides the opportunity to integrate a radiographic marker in an existing production process. Costs for an additional component are saved. There is no need for an additional adhesive step or welding process for attaching the radiographic marker.

The features disclosed in the description, claims, and figures may be relevant both individually and in any combination with one another for realizing embodiments.

The following is a summary list of reference numerals and the corresponding structure used in the above description of the invention:

1 Housing
2 Electrode connector device
3 Feedthrough
4 Antenna without radiographic marker
5 Antenna with radiographic marker
6 radiographic marker
7 Receiving device for plug
8 Conductor

The invention claimed is:

1. . An electrode connector device for an implant, the connector device comprising:
   a metal conducting element and a radiographic manufacturer identification tag integrated in said metal conducting element;
   wherein said metal conducting element is selected from the group consisting of:
   an antenna; and
   a conductor connected to a receiving device for a connector, said conductor connecting said receiving device to a feedthrough that is disposed on a housing of the implant.

2. The electrode connector device according to claim 1, wherein said metal conducting element is made of a biocompatible metal.

3. The electrode connector device according to claim 2, wherein said metal conducting element is made of niobium.

4. The electrode connector device according to claim 1, wherein said metal conducting element and said radiographic manufacturer identification tag have a uniform thickness.

5. The electrode connector device according to claim 4, wherein said metal conducting element and said radiographic manufacturer identification tag have a thickness of at least 50 µm.

6. The electrode connector device according to claim 1, wherein at least one of said metal conducting element or said radiographic manufacturer identification tag have a thickness of at least 50 µm.

7. The electrode connector device according to claim 1, wherein said radiographic manufacturer identification tag has a graphic symbol.

8. The electrode connector device according to claim 1, wherein said radiographic manufacturer identification tag has an alphanumeric symbol.

9. An implant, comprising;
   a housing;
   an electrode connector device configured on said housing;
   electronic components disposed in said housing; and a feedthrough disposed on said housing;

said electrode connector device including a metal conducting element, a manufacturer identification tag integrated in said metal conducting element, and a receiving device configured to receive an electrode lead;

wherein said metal conducting element is selected form the group consisting of:

an antenna; and a conductor connecting said receiving device to said electronic components via said feedthrough.

10. The electrode connector device according to claim 1, wherein said metal conducting element is said antenna.

11. The electrode connector device according to claim 1, wherein said metal conducting element is said conductor.

12. The implant according to claim 9, wherein said metal conducting element is said antenna.

13. The implant according to claim 9, wherein said metal conducting element is said conductor.

* * * * *